United States Patent [19]
Blackwood et al.

[11] Patent Number: 5,328,852
[45] Date of Patent: Jul. 12, 1994

[54] ANALYTICAL ASSAY

[75] Inventors: John J. Blackwood, Needham; Shai Inbar, Brookline, both of Mass.

[73] Assignee: PB Diagnostic Systems, Inc., Westwood, Mass.

[21] Appl. No.: 962,461

[22] Filed: Oct. 16, 1992

Related U.S. Application Data

[63] Continuation-in-part of Ser. No. 533,163, Jun. 4, 1990, abandoned.

[51] Int. Cl.⁵ ............... G01N 33/543; G01N 33/558
[52] U.S. Cl. ....................... 436/518; 356/243; 422/56; 422/57; 422/82.05; 435/3; 435/289; 435/290; 435/967; 436/169; 436/170; 436/528; 436/805
[58] Field of Search ............... 422/56–58, 422/67, 63, 82.05; 435/3, 289, 290, 808, 962, 967; 436/169, 170, 518, 528, 805; 356/243

[56] References Cited

U.S. PATENT DOCUMENTS

| | | | |
|---|---|---|---|
| 4,144,306 | 3/1979 | Figueras | 422/56 |
| 4,381,921 | 5/1983 | Pierce et al. | 436/535 |
| 4,457,893 | 1/1984 | Takekawa | 422/64 |
| 4,459,358 | 7/1984 | Berke | 436/170 |
| 4,832,488 | 5/1989 | Hirai et al. | 356/243 |
| 4,870,005 | 9/1989 | Akiyoshi et al. | 435/7 |
| 4,884,213 | 9/1989 | Iwata et al. | 364/497 |
| 5,043,143 | 8/1991 | Shaw et al. | 422/65 |
| 5,166,079 | 11/1992 | Blackwood et al. | 436/517 |

FOREIGN PATENT DOCUMENTS

| | | |
|---|---|---|
| 0097952 | 6/1983 | European Pat. Off. |
| 0278149 | 6/1987 | European Pat. Off. |
| 0305563 | 9/1987 | European Pat. Off. |

*Primary Examiner*—Toni R. Scheiner
*Assistant Examiner*—Christopher L. Chin
*Attorney, Agent, or Firm*—Gaetano D. Maccarone; Elliott Korsen; Barbara V. Maurer

[57] ABSTRACT

A method for determining the amount of an analyte in a sample fluid utilizing an assay element which comprises at least one reagent layer. The assay method includes the steps of optically reading a signal producing species, e.g., a fluorescent label, a first time prior to depositing the sample fluid on the assay element and a second time, at the same wavelength and in the same location within the assay element after the sample fluid has been applied to the assay element and the sample analyte has interacted with the reagent(s) present in the assay element. The first, or dry, reading is corrected for relative humidity and/or temperature variations.

17 Claims, 3 Drawing Sheets

ANALYTICAL ASSAY

CROSS-REFERENCE TO RELATED APPLICATIONS

This application is a continuation-in-part of prior copending application Ser. No. 533,163, filed Jun. 4, 1990 now abandoned

BACKGROUND OF THE DISCLOSURE

The present invention relates to assays for the determination of analytes in fluids and, more particularly, to a method for correcting the signal obtained for variations caused by relative humidity and/or temperature variations.

Many types of assay elements for the rapid analysis of analytes present in biological fluids are known in the art. Of particular interest are dry multilayer analytical elements to which a sample, e.g., a drop of blood, serum or plasma, is applied and allowed to migrate or diffuse to a reagent layer or layers. As a result of the interaction between the analyte and the reagent(s) present, a detectable change is brought about in the element corresponding to the presence of the analyte in the sample. The detectable change can be a color change which may be evaluated visually or read spectrophotometrically such as with a densitometer. In another scheme based on the presence of fluorescent-labeled biologically active species, a fluorescent output signal can be generated and read spectrofluorometrically. Such assay elements are of great interest because they can be adapted for use in automated analytical instruments.

In the automated analytical instruments a sample of a test fluid is typically provided in a sample cup and all of the assay method steps including pipetting of a measured volume of the sample onto an assay element, incubation and readout of the signal obtained as a result of the interaction(s) between the reagent(s) and the sample analyte are carried out automatically. The assay element is typically transported from one station, e.g., the pipetting station, to another, e.g., the optical read station, by a transport means such as a rotating carousel to enable the test steps to be carried out automatically. Further, in some instruments the pipetting and optical read steps are carried out while the assay element is in a temperature-controlled chamber. Such automated instruments can be operated in the batch mode, that is, a plurality of assays for the same analyte are carried out at the same time. Also, some instruments are capable of being operated in a random-access mode, that is, assays for a plurality of different analytes can be carried out at the same time.

Such automated analytical instruments are capable of processing many assay elements rapidly and it is necessary to achieve a very high level of precision for these assays. However, imprecisions in the results obtained can be caused by a number of factors. Commonly assigned, copending U.S. patent application Ser. No. 382,555, filed Jul. 19, 1989 now U.S. Pat. No. 5,156,079 discloses and claims an analytical method which utilizes dry multilayer assay elements. The method corrects for signal imprecisions caused by variations in reagent levels from assay element to assay element and other variations including those in instrument position response. Briefly, this method involves taking a first optical reading of the assay element prior to delivering sample fluid to the element and, after the fluid has been dispensed and the requisite interaction between the sample analyte and the reagent(s) has taken place, taking a second optical reading. The ratio of the second signal to the first signal is taken and compared with that for known amounts of the analyte to determine the amount of analyte in the fluid.

As the state of the art advances, however, additional difficulties may be encountered. For example, the optical signals obtained from various dry assay elements including multilayer assay elements can vary significantly depending upon the relative humidity of the environment in which the instrument is located. Typically, these diagnostic assay elements are packaged in moisture impermeable materials and the relative humidity inside the package maintained at a very low level, e.g., about 10%, so as to prolong the shelf life of the elements. The assay elements should be removed from the package just prior to use and inserted into the analytical instrument without being allowed to remain in the ambient environment for any extended length of time. However, it is apparent that the ambient environment will vary from location to location and also within a location over time. Therefore the relative humidity within the instrument will vary.

Dealing with relative humidity and temperature considerations in random access analyzers involves still another level of difficulty since the individual assay elements may reside in the instrument for different periods of time before the dry optical reading is taken. One approach to dealing with temperature considerations in such analyzers is to allow the assay element to remain in a temperature controlled chamber for the period of time necessary for the element to equilibrate with the chamber temperature. A possible approach to the relative humidity factor would be to take the dry reading only after a particular assay element has been in the instrument for a period of time sufficient to permit it to come to equilibrium with the relative humidity of the environment and to correct the reading based on the relative humidity as measured by a sensor. Such procedures are not entirely satisfactory because imposing such minimum time periods on the assay protocols would restrict the throughput rate of the instrument and would not permit the instrument to be operated in the most efficient manner.

It would be desirable therefore to have a method for compensating for optical signal imprecisions caused by relative humidity and/or temperature variations which offers a number of optional choices based on the manner in which the operator desires to practice the method. It would also be desirable to have such a method which can be practiced so as not to adversely affect the throughput rate of the analytical instrument. Further, it would be desirable to have such a method which would permit a random access automated analytical instrument to be operated in the most efficient manner possible.

SUMMARY OF THE INVENTION

These and other objects and advantages are accomplished in accordance with the invention by providing a method for determining the amount of a component in a sample fluid such as plasma, serum, whole blood, buffer, etc. The assay method is carried out with an assay element which includes at least one reagent layer. The signal generating species in the assay element is read optically a first time prior to delivering the sample fluid to the element. Subsequently, after the sample fluid has been dispensed to the assay element and the interaction between the sample analyte and the reagent(s) present in the element has taken place, the signal producing species is read optically a second time.

According to the method, the first, or dry, optical signal is corrected for relative humidity and/or temperature variations. Depending upon the manner in which the method is practiced, as will be discussed in detail below herein, in correcting the signal the method takes into consideration the temperature of the ambient environment in which the instrument is located at the time of the measurement and/or the relative humidity level of the environment at the time of the measurement together with the length of time that the assay element has been in the instrument.

The corrected dry optical signal and the second optical signal may be manipulated in any manner to determine the amount of analyte in the sample fluid. In one embodiment according to the invention the ratio of the second optical signal to the corrected first optical signal is taken and compared with that for known amounts of the analyte to determine the amount of analyte in the sample fluid. In another embodiment the corrected first optical signal can be subtracted from the second optical signal, or vice versa, to provide a value which can be compared with that for known amounts of the analyte.

By correcting the dry optical signal in accordance with the invention a number of choices are afforded to an operator since it is possible to compensate for relative humidity and/or temperature considerations based on the manner in which the operator desires to practice the method. The method permits an automated analytical instrument to be operated in a random access or batch mode without any adverse effect on the throughput rate of the instrument. Further, in one embodiment, the instrument can be operated in the most efficient manner possible since it is not necessary to wait any minimum period of time before taking the first optical reading nor is there any maximum period of time which can elapse before the first optical reading must be taken. In this embodiment processing of the various different assay modules can be carried out essentially independently of such time considerations.

In another embodiment the first reading is taken immediately after inserting the assay element into the instrument in which case it is necessary to correct the optical signal only for the ambient temperature since the assay element does not have time to undergo a change in relative humidity. Of course, in this embodiment it is necessary to insert the assay element into the instrument within a short period of time, e.g., up to about one minute, after removing it from the humidity controlled environment in which it is packaged. According to another embodiment the assay element can be allowed to reside in a temperature controlled chamber of an instrument for a period of time sufficient for the element to equilibrate with the chamber temperature before the first reading is made. In this embodiment the optical signal is corrected for relative humidity variations based on the relative humidity of the ambient environment and the period of time the assay element has been in the chamber.

In a preferred embodiment the assay method of the invention is carried out with an assay element which includes at least one reagent layer and a light-blocking layer. The light-blocking layer provides an optical bound/free separation of the signal-generating species as a function of the amount of analyte in the sample fluid. The first and second optical readings are carried out by irradiating the same layer of the assay element in both instances at the same wavelength. In this preferred embodiment correction of the optical signal compensates for variations in reagent levels because of variations in reagent layer thicknesses from element to element and for variations in the analytical instrument position response as well as relative humidity and/or temperature variations.

BRIEF DESCRIPTION OF THE DRAWINGS

For a better understanding of the invention as well as other objects and further features thereof, reference is made to the following detailed description of various preferred embodiments thereof taken in conjunction with the accompanying drawings wherein.

DESCRIPTION OF THE PREFERRED EMBODIMENTS

The assay elements which are utilized in the assay method of the invention may include any suitable signal-generating species. Any light radiation emitting or absorbing label, including a label which reacts with a reagent, which provides a detectable signal can be utilized as the signal-generating species. The label may be a fluorophore, a phosphor or a light absorbing material. The method may be practiced with any "dry" assay element including those which are made up of only one reagent layer carried by a support layer, so called "multilayer" assay elements which have at least one reagent layer and at least one other layer such as a light-blocking layer, a layer for receiving a signal-generating species liberated from another layer, etc.

Figure 1:
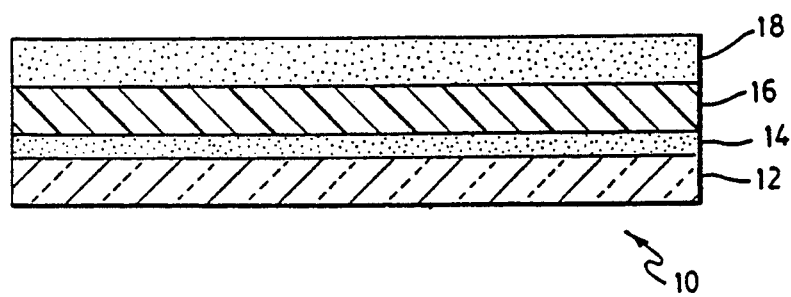
FIG. 1 is a partially schematic cross-sectional view of an assay element which can be utilized in the method of the invention.

The assay method of the invention will be described in detail with respect to a preferred embodiment of an assay element which may be utilized therein. Referring now to FIG. 1 there is seen an assay element 10 which is a thin film multilayer element typically having a thickness of about 0.1 mm and comprised of a transparent support 12 which carries in succession a reagent layer 14, a light-blocking layer 16 and an optional top coat layer 18 which may serve as a reagent layer, a filter layer such as for proteins, an anti-abrasion layer, etc. The reagent layer 14 is very thin, typically having a thickness of about 0.025 mm and includes an immunocomplex of a binding partner for the analyte of interest and a conjugate of a labeled analyte (the same as the sample analyte, an analogue thereof or a structurally similar material which will bind to the binding partner). The binding partner, an antibody when the sample analyte is an antigen, is immobilized in the reagent layer 14 by being covalently bound to the surface of the support layer 12, which may be of any appropriate material such as a polyester or a polystyrene, or to a matrix material or by being physically held by the matrix material. The matrix material may be a hydrophilic gel material such as gelatin, a polysaccharide, e.g., agarose, a derivatized polysaccharide, mixtures thereof, and the like. Light-blocking layer 16 may comprise any suitable material such as, for example, iron oxide, titanium dioxide or the like dispersed in a binder material such as a polysaccharide. The optional topcoat layer 18 may comprise an anti-abrasion layer of a material such as a polysaccharide or preferably may include buffers, blocking and displacing agents, etc.

The assay element 10 may also include a layer or other means (not shown) for distributing the sample fluid uniformly across the surface of the top layer of the element. Any suitable fluid distribution technique may be used including, for example, particulate layers, polymeric layers, fibrous layers, woven fabric layers and liquid transport systems which have been disclosed in the art as being suitable for this purpose. Many such liquid distribution systems and materials for providing a uniform distribution of a fluid sample across the surface of an assay element are known in the art and therefore extensive discussion of such materials and systems is not required here. A particularly preferred fluid transport system is that described in commonly assigned, copending application Ser. No. 210,732, filed Jun. 23, 1988 now U.S. Pat. No. 5,051,237. The distribution means, whether a layer of fibrous material, etc. or a liquid transport system is preferably relatively thick in comparison to reagent layer 14. In practice, the label which is present in reagent layer 14 is optically read prior to applying the sample to the assay element by irradiating layer 14 with the appropriate electromagnetic radiation through transparent support layer 12 to obtain a first readout signal.

According to the invention this first optical reading is corrected for relative humidity and/or temperature variations. As noted previously, the reading can be corrected for either temperature variations or relative humidity variations or both. Typically, the reading is taken while the assay element resides in a temperature controlled chamber within an automated instrument. To correct for temperature variations the temperature of the ambient environment in which the instrument is located is used. The correction for relative humidity is based on the actual relative humidity level of that environment at the time the measurement is taken and the period of time the assay element has been in the instrument. Accordingly, the ambient temperature and relative humidity and the amount of time the assay element is within the instrument are the variables which are taken into account in the correction of the dry reading.

To further aid those skilled in the art to understand and practice the invention, the proposed theoretical mechanism by which the dry reading is affected by relative humidity will be discussed. The proposed theoretical mechanism appears to explain the varying optical signals which were obtained from actual experiments as a result of relative humidity and temperature variations. It should be understood, however, that the advantageous results which are provided by the method of the invention have been observed through extensive experimentation and therefore the proposed theoretical mechanism is not to be construed as limiting of the invention.

Consider the situation where the assays are being carried out by means of an automated analytical element wherein a plurality, for example, seventeen assay elements are inserted into the temperature controlled chamber of the instrument and all the steps of the assay method performed while the assay elements reside therein. For purposes of illustration consider also that the assay elements are all for the determination of the same analyte, for example, theophylline. An experiment was conducted by first calibrating the instrument at 20% relative humidity with a set of theophylline calibrators and storing the calibration curve. It should be noted here that this experiment was carried out at constant room temperature; the temperature dependence of the optical signals will be discussed below. Subsequently, while in the 20% relative humidity environment, seventeen theophylline assay elements were loaded into the temperature controlled chamber and processed. The instrument batched the assay elements such that the first fourteen assays were completed, that is, a dry reading taken, the control solution deposited and a second reading taken, prior to taking the first dry readings of the other three assay elements. Accordingly, assay elements 15-17 remained in the chamber for some period of time before the first dry readings of these elements were taken. The same theophylline control solution was applied to all the assay elements. Thus, the dose result was expected to be the same (within precision) for all the elements. The dose results obtained are shown in Table I. It is seen that an "end" effect was observed with assay elements 15-17 because of the delay in their processing and that these assay elements gave higher dose results than the others for the same sample fluid. At 20% relative humidity the mean of the readings for the last three assay elements was 11.7 mg/l compared to an overall mean of 11.0 mg/l.

The instrument was then transferred to an 80% relative humidity environment and the procedure repeated with seventeen new assay elements using the same control theophylline solution. It is seen that the uncorrected dose results had a mean value of 13.8 mg/l and, further, that the dose results increase progressively with the period of time the particular assay element remained in the chamber before the first dry reading was taken. Accordingly, at constant temperature, the "end" effect was shown to be the result of a slow rise in the dry reading during incubation due to humidity.

Figure 2B:
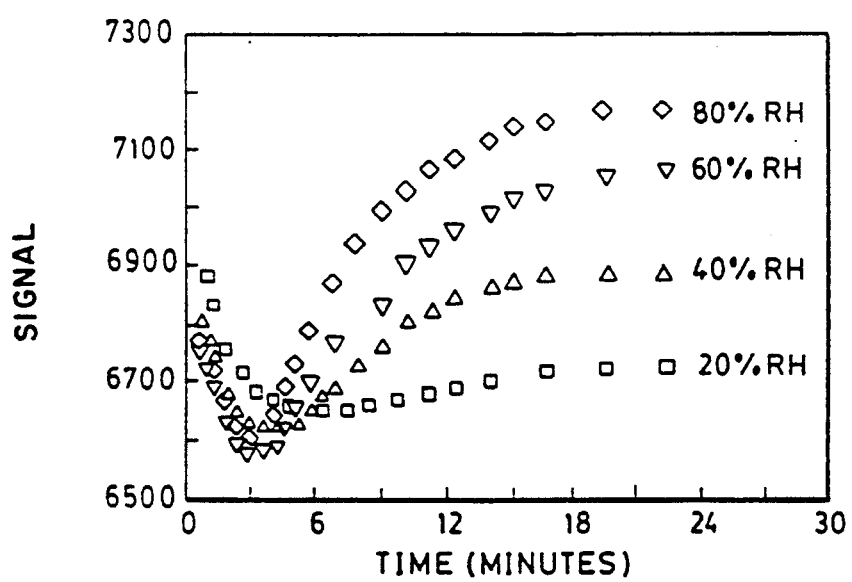
FIG. 2B is a graphical illustration showing the dry reading optical signals obtained over a period of time with assay elements residing in a temperature controlled chamber at different relative humidity levels.
Figure 2A:
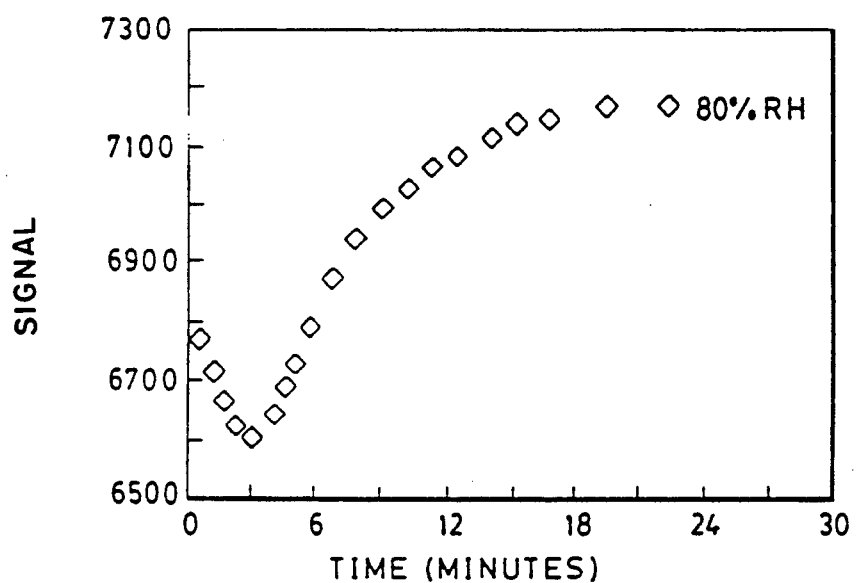
FIG. 2A is a graphical illustration showing the dry reading optical signals obtained over a period of time in an 80% relative humidity experiment with one assay element.

To correct for this condition it was thought to be necessary to have the appropriate relationship between the dry reading, time, relative humidity and temperature and therefore the kinetics of the dry reading had to be ascertained. To study these kinetics a single assay element was loaded into the temperature controlled chamber of the instrument in the 80% relative humidity environment and dry readings taken every thirty seconds beginning immediately. The dry readings initially decreased with time until a minimum was reached (about three minutes) and after a delay increased to a constant level when equilibrium was reached (about twenty to twenty five minutes). The results are shown in FIG. 2A. The same phenomenon was observed at other relative humidity levels except that the final readings decrease with decreasing relative humidity as shown in FIG. 2B. The room temperature was the same during all these experiments (22° C.).

Upon examination of the observed curves shown in FIGS. 2A and 2B it was theorized that they are the result of two different phenomena, namely a temperature effect and a humidity effect. It is apparent that when the assay element is inserted into the temperature controlled chamber, its temperature begins to rise from that of the ambient environment toward the chamber temperaure, typically 37° C. Since the fluorescence of the dye used as a label is inversely related to temperature, the intensity of the dry reading will decrease as the temperature of the assay element increases until an equilibrium is reached when the assay element reaches the temperature of the chamber.

The equilibrium from lower temperature to an higher temperature is a first order process of the type $$A \xrightarrow{k_T} B$$

The mathematical expression for such kinetics is $$dM/dt = k_T A \quad B = B_o + A e^{-k_T t}$$

where $B_o$ is the final fluorescence intensity (at 37° C.), A is the difference in intensity between room temperature and 37° C., $k_T$ is the rate constant associated with the method and t is time.

For the specific case under consideration the equation for the temperature effect is $$D_{T(t)} = D_{37°} + (D_{RT} - D_{37°})e^{-k_T t}$$

where $D_{T(t)}$ is the dry reading as a function of time due to the temperature effect, $D_{37°}$ is the dry reading at equilibrium (37° C.) and $D_{RT}$ is the dry reading at room temperature, all of the above in a constant relative humidity (the package relative humidity).

In considering the humidity effect it was thought that a two part mechanism was responsible for the changes in the dry reading because of humidity variations. First, it was thought that the water vapor has to penetrate through the upper layers and reach the reagent, or signal, layer (14 in FIG. 1) before the dry reading is affected since this layer is the only one irradiated to obtain the optical reading. Thus, a certain time delay was expected before the onset of the humidity effect.

Secondly, it was theorized that once the water vapor reaches the signal layer a double kinetics follows: 1) water arriving at a certain rate to the layer; and 2) water reacting in a way as to cause a change in fluorescence. Although the exact cause of the change was not clear, the kinetics behavior of the change was expected to follow the pattern of:

$$A \xrightarrow{k_1} B \xrightarrow{k_2} C$$

The mathematical expression for such kinetics is $$dB/dt = k_1 A \quad dC/dt = k_2 B$$

$$C_{(t)} = C_o + B[1 + (k_1 e^{-k_2 t} - k_2 e^{-k_1 t})/(k_2 - k_1)]$$

where $C_{(t)}$ is the dry reading as a function of time, $C_o$ is the initial dry reading (at the package humidity), B is the difference between the dry reading at package humidity and room humidity, t is the time and $k_1$ and $k_2$ are the two rate constants associated with the process.

In the specific case being considered the equation can be written $$D_{RH(t)} = D_{PK} + (D_{RH} - D_{PK})[1 + (k_1 e^{-k_2 t} - k_2 e^{-k_1 t})/(k_2 - k_1)]$$

where $D_{RH(t)}$ is the dry reading as a function of time as affected by the humidity change, $D_{PK}$ is the dry reading at the package humidity and $D_{RH}$ is the dry reading at room humidity.

To account for the time delay, $t_D$, the equation is modified somewhat to:

For $t > t_D$ $$D_{RH(t)} = D_{PK} + (D_{RH} - D_{PK})[1 + (k_1 e^{-k_2(t - t_D)} - k_2 e^{-k_1(t - t_D)})/(k_2 - k_1)]$$

For $t < t_D \quad D_{RH(t)} = 0$

The constants $D_{PK}$ and $D_{37°}$ are in fact referring to the same quantity and are identical. This quantity can be labeled as $D_o$, the value that must be calculated for each assay element and used for the dry reading correction. The equation provides a signal which is initially constant and then rises until it reaches equilibrium.

The overall behavior of the assay elements is the sum of the two processes and is given by the combined equation $$D_{RH,T(t)} = D_o + (D_{RT} - D_o)e^{-k_T t} + (t > t_D)(D_{RH} - D_o)[1 + (k_1 e^{-k_2(t - t_D)} - k_2 e^{-k_1(t - t_D)})/(k_2 - k_1)]$$

wherein $D_o$ is the "basic" dry reading for the assay element (this is the dry reading that would have been obtained at the chamber if there were no humidity effect; this value must be calculated according to the equation), $D_{RT}$ is the initial dry reading at the moment of inserting the assay element into the chamber; $D_{RH}$ is the final dry reading in the chamber after the assay element is equilibrated for both the incubator temperature and the ambient humidity; $t_D$ is the delay time for the onset of the humidity effect; $k_t$ is the rate constant for the assay element thermal equilibrium in the chamber; $k_1$ is the first rate constant for the effect of humidity on the dry reading; $k_2$ is the second rate constant for the effect of humidity on the dry reading; and $t > t_D$ is a logical expression that is equal to 0 when $t < t_D$ and equal to 1 when $t > t_D$.

The final kinetics pattern is the result of adding the two curves according to the two phenomena. The resulting curve closely resembles those obtained experimentally (FIGS. 2A and 2B).

Establishing the values for the equation parameters involves fitting the experimental data to the equation described above. Experimental data were obtained with many assay elements for different analytes and from different production lots. Each set of data produced a set of constants and after testing all the sets in the experimental study, an average was taken.

The experimental data can be fit to the equation by means of a computer program. The program can find the equation constant values for each of the experimental sets that give the best fit between the experimental and the theoretical results. An experimental data set is entered into the computer and the best fit is found by a semi-interactive process. A program for providing the best fit can be based on a grid search where each of the constants is tested over a range with many discreet values inside the range. The best fit can be judged by the least square method. The ranges of the search for each constant can be decided by initial estimates made by the user.

The constant $k_t$, $k_1$ and $k_2$ are expected to be independent of humidity and temperature and once their values are established over many assay runs, an average can be calculated and used in the equation, $D_{RT}-D_o$, which can be expressed as $\Delta D_T$, is expected to be humidity independent as long as the assay elements are loaded into the instrument immediately after opening the package (about one minute or less); it is expected to be room temperature dependent. The dependence on temperature was shown to be linear in the form of $$\Delta D_T = A_T \cdot T + B_T$$

where $A_T$ and $B_T$ are constants which are found experimentally.

$D_{RH}-D_o$, which can be expressed at $\Delta D_{RH}$, is temperature independent and depends on humidity in a close to linear fashion as established experimentally. In the final form of the equation this expression is entered as a function of the measured relative humidity, $$t_D = C_1 \cdot RH^{-C_2}$$

The final equation containing only time (t), temperature (T) and relative humidity (RH) as variables is $$D_{(t,RH,T)} = D_o + (A_T \cdot T + B_T)e^{-kT_t} +$$
$$(t > C_1 \cdot RH^{-C_2}) \cdot (A_r \cdot RH + B_r) \cdot [1 + (k_1 e^{-k_2(t-C_1 \cdot RH^{-C_2})} -$$
$$k_2 e^{-k_1(t-C_1 \cdot RH^{-C_2})})/(k_2 - k_1)]$$

where $D_{(t,RH,T)}$ is the dry reading at a time, t, a humidity, RH, and a room temperature, T.

The dry reading, $D_o$, to be used for normalization can be calculated from the equation $$D_o = D_{(t,RH,T)} - (A_T \cdot T + B_T)e^{-kT_t} -$$
$$(t > C_1 \cdot RH^{-C_2}) \cdot (A_r \cdot RH + B_r) \cdot [1 + (k_1 e^{-k_2(t-C_1 \cdot RH^{-C_2})} -$$
$$k_2 e^{-k_1(t-C_1 \cdot RH^{-C_2})})/(k_2 - k_1)]$$

Figure 3:
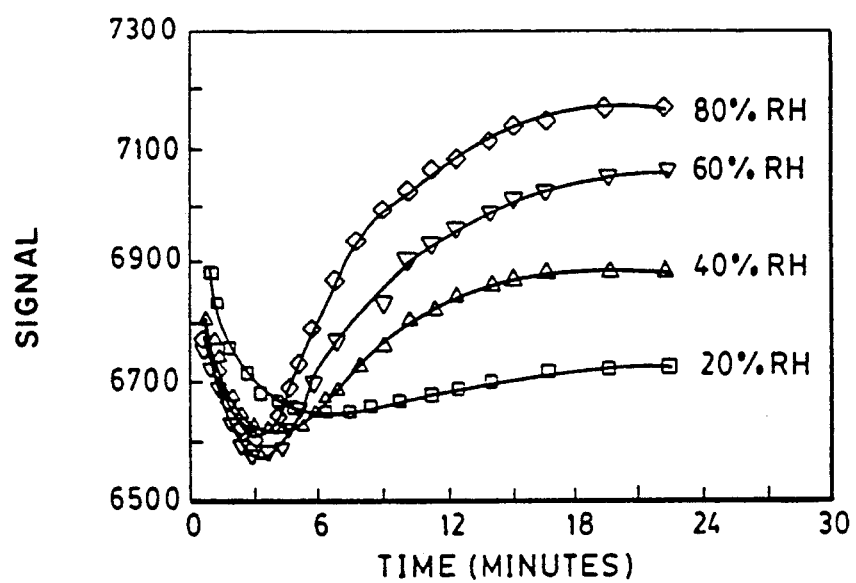
FIG. 3 is a graphical illustration showing the comparison of the experimental results (data points) shown in FIG. 2B to the results calculated (solid lines) from a mathematical equation developed as a result of a proposed theoretical mechanism.

FIG. 3 shows the comparison of the experimental results shown in FIG. 2B with the curves calculated from the equation using constants obtained with a computer program. The constants found were: $A_r = 9.7$; $B_r = -102$; $A_T = -75$; $B_T = 1950$; $C_1 = 94$; $C_2 = 0.85$; $K_T = 0.85$; $K_1 = 0.24$; $K_2 = 0.55$.

It is seen that the fit between the experimental results and the theoretical equation is excellent and supports the proposed mechanism.

The equation in this form was used to correct the data which illustrated the "end" effect. The corrected dose results are shown in Table I and clearly demonstrate that the "end" effect was eliminated by the method of the invention. For the 20% relative humidity results it can be seen that the mean value for assay elements 15-17 was 10.8 mg/l, the same as the overall corrected mean value and the CV decreased to 1.72%. For the 80% relative humidity results the overall corrected mean value was 10.7 mg/l and the CV decreased to 5.31%.

TABLE I

| Assay Element | 20% RH Theophylline (mg/l) | | 80% RH Theophylline (mg/l) | |
|---|---|---|---|---|
| | Uncorrected | Corrected | Uncorrected | Corrected |
| 1 | 10.8 | 10.6 | 12.6 | 10.9 |
| 2 | 11.0 | 10.8 | 12.7 | 10.8 |
| 3 | 10.9 | 10.8 | 13.0 | 10.9 |
| 4 | 10.7 | 10.6 | 13.2 | 11.0 |
| 5 | 10.7 | 10.6 | 12.9 | 10.6 |
| 6 | 10.8 | 10.7 | 12.7 | 10.3 |
| 7 | 10.8 | 10.7 | 12.8 | 10.1 |
| 8 | 10.8 | 10.4 | 13.3 | 10.5 |
| 9 | 10.5 | 10.8 | 14.3 | 11.3 |
| 10 | 10.9 | 11.0 | 13.7 | 10.7 |
| 11 | 11.0 | 10.9 | 12.1 | 9.1 |
| 12 | 10.9 | 11.3 | 13.6 | 10.4 |
| 13 | 11.3 | 10.8 | 15.7 | 11.3 |
| 14 | 10.8 | 10.8 | 15.8 | 11.3 |
| 15 | 11.7 | 10.7 | 16.1 | 11.6 |
| 16 | 11.6 | 10.9 | 15.2 | 10.8 |
| 17 | 11.9 | 10.9 | 14.9 | 10.6 |
| Mean (mg/l) | 11.0 | 10.8 | 13.8 | 10.7 |
| SD | 0.4 | 0.2 | 1.3 | 0.6 |
| % CV | 3.41 | 1.72 | 9.21 | 5.31 |

In view of the foregoing it will be appreciated that by correcting the dry reading of an assay element in accordance with the invention using temperature, relative humidity and time as variables, the effect of relative humidity and temperature on the results obtained can be substantially eliminated. The relative humidity value at the time of the actual dry reading can be conveniently obtained by means of a relative humidity sensor arranged in the analytical instrument. It is preferred to locate the relative humidity sensor inside the instrument but outside the temperature controlled chamber in instances where fluid is dispensed to the assay elements while they reside in the chamber since the dimensions of the chamber and the frequency of dispensing of fluids can cause rapid, relatively large relative humidity variations within the chamber that are not followed as quickly by the test element. It has been found in such situations that sensing the relative humidity outside the chamber will provide the advantageous results according to the invention. The relative humidity sensor can be conveniently coupled to a microprocessor so as to transmit the relative humidity readings to the microprocessor continuously. Of course, the elapsed time that the assay element has been in the chamber is also conveniently continuously monitored by the microprocessor.

According to the method of the invention, after the dry reading is taken the sample fluid is then distributed across the surface of the assay element and the fluid diffuses throughout layers 14, 16 and 18 as well as any fluid distribution layer or liquid transport system present and an equilibrium is established. The analyte present in the sample will compete with the labeled analyte in reagent layer 14 for the available binding sites on the antibodies immobilized in layer 14, the labeled analyte being dissociated therefrom and replaced by the sample analyte in a ratio appropriately equal to the relative amounts of sample analyte and labeled analyte. Thus, depending upon the amount of analyte in the sample, some percentage of the labeled analyte initially bound to the immobilized antibodies in layer 14 will be displaced therefrom and distributed throughout the remainder of the assay element. The amount of labeled analyte bound to the immobilized antibodies in reagent layer 14 at any time is inversely proportional to the amount of sample analyte.

A second readout signal is obtained by again irradiating reagent layer 14 through support layer 12 with the same electromagnetic radiation used in the first optical read step to obtain a second signal which is inversely proportional to the amount of sample analyte, that is, the signal decreases as the amount of sample analyte increases. Since reagent layer 14 is relatively thin in comparison to the combined thickness of layers 16 and 18 together with that of any fluid distribution layer or liquid transport system present and because light blocking layer 16 prevents any of the readout electromagnetic radiation from entering layer 18 or anything above it, the second signal obtained will be a function of the labeled analyte which is bound to the immobilized antibodies and a small percentage of the free labeled analyte which is distributed throughout the remainder of the assay element. In a preferred embodiment the ratio of the thickness of reagent layer 14 to the combined thickness of the light-blocking layer and the remainder of the assay element is from about 1:20 to about 1:100 or more.

As described previously, the corrected first, or dry, optical signal and the second optical signal can be manipulated in any manner to determine the amount of analyte in the sample fluid. The manner in which these readings are manipulated is determined by the type of assay element used in any instance and the types of variations sought to be compensated for by taking the first, or dry, reading.

In a preferred embodiment, the ratio of the second signal to the first signal is taken and compared with that for known amounts of the analyte to determine the amount of analyte in the sample fluid. The ratio may be used as obtained or it may be multiplied by some constant, dependent upon the particular assay, to provide a signal which falls in some desired range.

In another embodiment the corrected first optical signal can be subtracted from the second optical signal, or vice versa. By obtaining a first, or dry, optical signal as well as a second optical signal correction can be made for signal imprecisions caused by variations in reagent levels from assay element to assay element and other variations including those in instrument position response.

Generally, it is preferred to divide, or obtain the ratio, of the corrected first optical signal and the second optical signal where the variations are found to be relative, that is, where the optical readings obtained with different assay elements or at different positions on the instrument differ by the same percentage. It is preferred to subtract the readings when the variations are found to be absolute, that is, when the readings differ from each other by the same amount.

It will be appreciated that the method of the invention can be practiced according to a number of embodiments thereof. In one, the method can be practiced such that it is necessary to correct for temperature only by removing the assay element from a relative humidity controlled environment, for example, its package, inserting it into the instrument within a very short period of time, for example, a minute or less and taking the first dry reading immediately. In another embodiment the method can be practiced in a manner such that it is necessary to correct only for relative humidity by allowing the assay element to remain in a temperature controlled chamber for the period of time required for the element to equilibrate with the chamber temperature. In still another embodiment the method can be practiced without regard to any such minimum or maximum time considerations and the optical signal corrected for relative humidity and temperature. According to this embodiment the method of the invention can be carried out in the most efficient manner permitted by the particular instrumentation used to carry out the assay. Since it is not necessary to wait for any minimum length of time to take the dry reading and, on the other hand, the dry reading can be taken after any amount of time has elapsed after the assay element has been inserted into the temperature controlled chamber, a plurality of assay elements may be processed simultaneously and the sequence of steps practiced with each assay element determined according only to factors which result in the most efficient operation of the instrumentation. While it will be appreciated that this is so for batch processing of a plurality of assay elements for testing for the same analyte, the method of the invention is particularly advantageous for random access processing, that is, where assay elements for testing for different analytes are processed simultaneously and, further, individual ones of the assay elements are removed from the instrument when the particular assay is complete and others inserted in their places while still others remain in the chamber because the particular assay is not yet finished. This capability of an instrument to handle a plurality of different assay elements for different analytes having varying assay protocols, permits the instrument to be operated in a very efficient mode and advantageously allows the throughput of the instrument to be maximized. In accordance with the practice of the method, variations in the instrument position response and in the thickness of the reagent layer(s) from assay element to assay element as well as relative humidity and/or temperature variations can be compensated for and significantly better precision obtained.

The invention will now be discribed further in detail with respect to specific preferred embodiments by way of examples, it being understood that these are intended to be illustrative only and the invention is not limited to the materials, procedures, etc. recited therein.

EXAMPLE I

An assay element was prepared comprising a transparent polyethylene terephthalate support having coated thereon in succession:

1. a reagent layer comprising about 500 mg/m$^2$ of a 3:1 mixture of agarose and glyoxyl agarose; about 72 mg/m$^2$ of bis tris propane buffer; about 10 mg/m$^2$ of an antibody raised against theophylline; and about 0.07 mg/m$^2$ of a fluorescent labeled theophylline conjugate represented by the formula

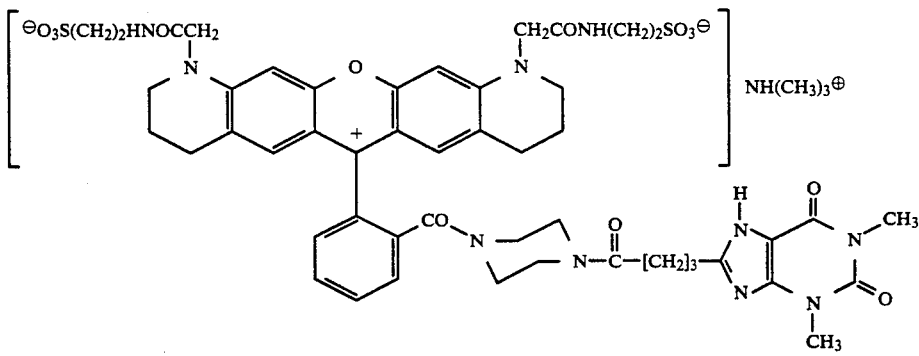

2. a light-blocking layer comprising about 6000 mg/m² of iron oxide, about 2000 mg/m² of agarose and about 50.4 mg/m² of 2'-morpholino ethane sulfonic acid (pH 5.7); and 3. a topcoat layer comprising about 2000 mg/m² of agarose.

Seventeen such assay elements were inserted one after the other into a temperature controlled chamber (37° C.) of an automated laboratory instrument. First and second readings of the assay elements were taken by irradiating the assay element through the transparent support with 550 nm excitation energy and the fluorescent emissions measured at 580 nm. The instrument processed the assay elements in the manner described above herein. Similar experiments were carried out at 20% and 80% relative humidity, respectively. The uncorrected results, together with those obtained by correcting these results in accordance with the invention, are shown in Table I.

Although the invention has been described with respect to specific preferred embodiments, it is not intended to be limited thereto but rather those skilled in the art will recognize that variations and modification may be made therein which are within the spirit of the invention and the scope of the appended claims.

What is claimed is:

1. A method for determining an analyte in a sample fluid consisting essentially of
   (a) irradiating a region of an assay element including a signal generating species with electromagnetic radiation to obtain a first optical signal prior to applying any sample fluid to said assay element;
   (b) correcting said first optical signal for relative humidity and/or temperature variations with an equation which utilizes temperature, relative humidity and time as variables to determine a basic dry reading, $D_o$;
   (c) applying a sample fluid to said assay element;
   (d) allowing analyte in said sample fluid to react with said signal generating species;
   (e) irradiating said assay element in the same region and with the same electromagnetic radiation utilized in step (a) to obtain a second optical reading; and
   (f) determining the amount of analyte in said sample fluid as a function of said basic dry reading and said second optical reading.

2. The method as defined in claim 1 wherein said assay element comprises (i) a light-blocking layer which is permeable to said sample fluid and which overlies (ii) a reagent layer, said signal generating species residing in said reagent layer; step (a) comprises irradiating said reagent layer with electromagnetic radiation; step (e) comprises irradiating said reagent layer with the same electromagnetic radiation utilized in step (a); and step (f) comprises taking a ratio of said second optical reading to said basic dry reading and comparing said ratio with those obtained for known amounts of said analyte.

3. The method as defined in claim 2 wherein said assay element further includes a support which is transparent to said electromagnetic radiation, said support underlying said reagent layer.

4. The method as defined in claim 2 wherein said reagent layer includes an immobilized binding partner for said analyte and said signal generating species comprises a conjugate of a label bound to a moiety which is capable of binding to said binding partner.

5. The method as defined in claim 4 wherein said moiety bound to said label is said analyte or an analogue thereof.

6. The method as defined in claim 4 wherein said label is fluorescent.

7. The method as defined in claim 1 wherein step (b) comprises correcting said first optical signal for relative humidity and temperature variations.

8. The method as defined in claim 1 wherein step (b) comprises correcting said first optical signal for relative humidity variations.

9. The method as defined in claim 1 wherein step (b) comprises correcting said first optical signal for temperature variations.

10. A method for processing a plurality of assay elements in an analytical instrument consisting essentially of
    (a) inserting a plurality of assay elements into a temperature controlled chamber of an analytical instrument;
    (b) irradiating at least one of said assay elements in a region thereof which includes a signal generating species with electromagnetic radiation to obtain a first optical signal for said assay element prior to applying any sample fluid to said element;
    (c) correcting said first optical signal for said assay element for relative humidity and/or temperature variations with an equation which utilizes temperature, relative humidity and time as variables to determine a basic dry reading, $D_o$;
    (d) applying sample fluid to said assay element;
    (e) allowing analyte in said sample fluid to react with said signal generating species;
    (f) irradiating said assay element in the same region and with the same electromagnetic radiation utilized in step (b) to obtain a second optical reading for said element; and (g) determining the amount of analyte in said sample fluid as a function of said basic dry reading and said second optical reading.

11. The method as defined in claim 10 wherein step (c) comprises correcting said first optical signal for each said assay element for relative humidity variations.

12. The method as defined in claim 10 wherein step (c) comprises correcting said first optical signal for each said assay element for temperature variations.

13. The method as defined in claim 10 wherein step (c) comprises correcting said first optical signal for relative humidity and temperature variations.

14. The method as defined in claim 10 wherein said assay element comprises (i) a light-blocking layer which is permeable to said sample fluid and which overlies (ii) a reagent layer, said signal generating species residing in said reagent layer, and step (g) comprises taking a ratio of said second optical reading to said basic dry reading and comparing said ratio with those obtained from known amount of said analyte.

15. The method as defined in claim 14 wherein said reagent layer includes an immobilized binding partner for said analyte and said signal generating species comprises a conjugate of a label bound to a moiety which is capable of binding to said binding partner.

16. The method as defined in claim 15 wherein said moiety bound to said label is said analyte or an analogue thereof.

17. The method as defined in claim 16 wherein said label is fluorescent.

* * * * *